United States Patent [19]

Langbein et al.

[11] 4,069,331

[45] Jan. 17, 1978

[54] N-(P-FLUOROBENZOYL-N-PROPYL)-4-PIPERIDYLAMIDES AND SALTS THEREOF

[75] Inventors: Adolf Langbein, Ingelheim am Rhine; Peter Danneberg, Ockenheim; Franz Josef Kuhn, Bingen am Rhine, all of Germany

[73] Assignee: Boehringer Ingelheim GmbH, Ingelheim am Rhine, Germany

[21] Appl. No.: 760,001

[22] Filed: Jan. 17, 1977

[30] Foreign Application Priority Data

May 16, 1974 Germany ................................ 2423897

Related U.S. Application Data

[63] Continuation-in-part of Ser. No. 664,761, March 8, 1976, abandoned, which is a continuation-in-part of Ser. No. 575,940, May 9, 1975, abandoned.

[51] Int. Cl.² .......................................... C07D 211/58
[52] U.S. Cl. ................................ 424/267; 260/293.77
[58] Field of Search ................... 260/293.77; 424/267

[56] References Cited

U.S. PATENT DOCUMENTS

3,161,637  12/1964  Janssen ........................... 260/293.77

FOREIGN PATENT DOCUMENTS

1,345,872  2/1974  United Kingdom ............ 260/293.77

*Primary Examiner*—Norma S. Milestone
*Attorney, Agent, or Firm*—Hammond & Littell

[57] ABSTRACT

Compounds of the formula

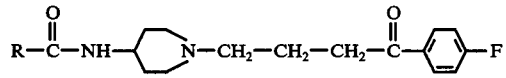

wherein R is straight or branched alkyl of 1 to 4 carbon atoms, and non-toxic, pharmacologically acceptable acid addition salts thereof; the compounds as well as their salts are useful as sedatives and tranquilizers.

10 Claims, No Drawings

N-(P-FLUOROBENZOYL-N-PROPYL)-4-PIPERIDYLAMIDES AND SALTS THEREOF

This is a continuation-in-part of copending application Ser. No. 664,761 filed Mar. 8, 1976, now abandoned which in turn is a continuation-in-part of application Ser. No. 575,940, filed May 9, 1975, now abandoned.

This invention relates to novel N-(p-fluorobenzoyl-n-propy) -4-piperidylamides and acid addition salts thereof, as well as to methods of preparing these compounds.

More particularly, the present invention relates to a novel class of N-(p-fluorobenzoyl-n-propyl)-4-piperidylamides represented by the formula

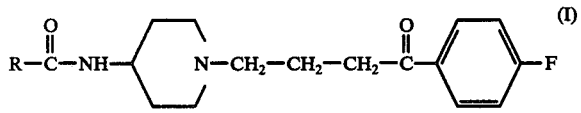

(I)

wherein R is alkyl of 1 to 4 carbon atoms, and non-toxic, pharmacologically acceptable acid addition salts thereof.

the compounds embraced by formula I above may be prepared by the following methods.

METHOD A

By alkylating a 4-amido-piperidine of the formula

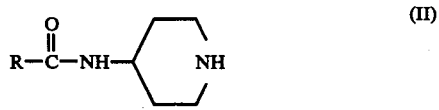

(II)

wherein R has the same meanings as in formula I, or an acid addition salt thereof, with a p-fluoro-butyrophenone of the formula

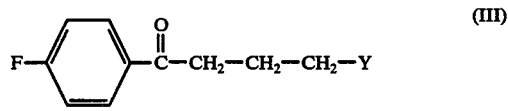

(III)

wherein Y is halogen, especially chlorine, bromine or iodine, phenylsulfonyl, toluenesulfonyl, alkylsulfonyl or the like.

The alkylation is carried out in conventional manner, preferably in the presence of an acid-building agent, with the starting compound of the formula III being provided in the stoichiometric amount or in excess thereof. Examples of suitable acid-binding agents are triethylamine, N, N-dicyclohexyl-ethylamine, sodium carbonate, potassium carbonate, calcium oxide or, preferably, sodium bicarbonate.

Although the performance of the reaction in a solvent medium is not absolutely essential, it is advantageous to add an inert solvent to the reaction mixture. Examples of suitable inert solvents are lower alkanols, chloroform, toluene, nitromethane, tetrahydrofuran or, preferably, dimethylformamide; mixtures of any two or more of these solvents may also be used.

The optimum alkylation reaction temperature may vary within wide limits, depending upon the reactivity of the reactants, but generally lies between 50° and 150° C. However, the reflux temperature of the reaction mixture is preferred.

the addition of from catalytic to molar amounts of potassium iodide or sodium iodide to the reaction mixture is of advantage in some instances.

METHOD B by acylating 4-(N'-amino-piperidino)-p-fluorobutyrophenone of the formula

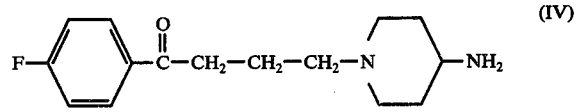

(IV)

with a carboxylic acid derivative of the formula

(V)

wherein R has the same meanings as in formula I, and X is halogen, preferably chlorine, or —CO—R, where R has the meanings previously defined.

The reaction is preferably carried out in an inert solvent comprising polar functional groups, such as benzene, chloroform, acetonitrile, dioxane, tetrahydrofuran, dimethyl sulfoxide, dimethylacetamide or, preferably dimethylformamide.

In this case, too, the reaction is generally enhanced by the addition of an acid-binding agent. Examples of suitable acid-binding or basic condensation agents are alkali metal or alkaline earth metal hydroxides, carbonates or bicarbonates, such as sodium hydroxide, potassium hyfroxide, calcium hydroxide, sodium carbonate, potassium carbonate, potassium bicarbonate or, preferably, sodium bicarbonate; alkali metal acetates or alcoholates; tertiary organic bases, such as trimethylamine or triethylamine; or pyridine.

The acylation may also be effected with a free carboxylic acid of the formula V(X=H), but in that case the presence of a dehydrating condensation agent, such as dicyclohexyl-carbodiimide, is required.

The optimum temperature for the acylation reaction depends largely upon the starting compounds which are used; in general, however, it lies between 20° and about 100° C, but the reflux temperature of the solvent medium is preferred.

The compounds embraced by formula I are organic bases and therefore form acid addition salts with inorganic or organic acids. Examples of non-toxic, pharmacologically acceptable acid addition salts are those formed with a hydrohalic acid, nitric acid, sulfuric acid, orthophosphonic acid, oxalic acid, citric acid, tartaric acid, fumaric acid, maleic acid, propionic acid, butyric acid, acetic acid, methanesulfonic acid, toluenesulfonic acid, sulfonilic acid, succinic acid, 8-chlorotheophylline or the like.

The starting compounds of the formulas II, III, IV and V are known compounds. For example, the compounds of the formula II are disclosed in German Offenlegungsschrift No. 2,341,376; and the compounds of the formula III are disclosed in U.S. Pat. No. 2, 985,657.

The following examples illustrate the present invention and will enable others skilled in the art to understand it more completely. It should be understood, however, that the invention is not limited solely to the particular examples given below.

EXAMPLE 1

N-[3'-(p-Fluoro-benzoyl)-n-propyl]-4-piperidylacetamide and its hydrochloride by method A A mixture consisting of 3.57 gm (20 millimols) of 4-acetamidopiperidine hydrochloride, 4.02 gm (20 millimols) of ω-chloro-p-fluorobutyrophenone, 2.52 gm (30 millimols) of sodium bicarbonate, 3.32 gm (20 millimols) of sodium iodide and 50 ml of dimethylformamide was stirred at a temperature of 100° C for 2 hours, and the suspension obtained thereby was evaporated at 70° C as far as possible. The residue was taken up in a mixture of 250 ml of methylene chloride and 100 ml of water, and the organic phase was subsequently extracted 5 times with 125 ml each of water. After drying over sodium sulfate, the organic phase was suction-filtered and the filtrate was evaporated. The residue was a yellowish oil, which was dissolved in 15 ml of ethanol, the solution was admixed with 5 ml of 4 N ethanolic hydrochloric acid and subsequently with 60 ml of ether. 3 gm (43.8% of theory) of the hydrochloride of the formula

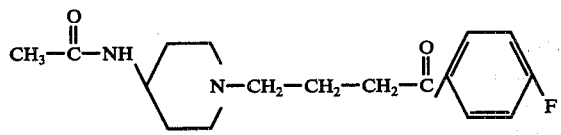

having a melting point of 179°–181° C were obtained.

EXAMPLE 2

Using a procedure analogous to that described in Example 1, N-[3'-(p-fluoro-benzoyl)-n-propyl]-4-(propionyl-amino) -piperidine and its hydrochloride, m.p. 173–175° C, were prepared from 4-(propionyl-amino)-piperidine hydrochloride and ω-chloro-p-fluoro-butyrophenone.

EXAMPLE 3

Using a procedure analogous to that described in Example 1, N-[3'-(p-fluoro-benzoyl)-n-propyl]-4-(n-butyryl-amino) -piperidine and its hydrochloride, m.p. 174°–178° C, were prepared from 4-(n-butyryl-amino)-piperidine hydrochloride and ω-chloro-p-fluoro-butyrophenone.

EXAMPLE 4

Using a procedure analogous to that described in Example 1, N-[3'-(p-fluoro-benzoyl)-n-propyl]-4-(isobutyryl-amino) -piperidine and it hydrochloride, m.p. 220°–224° C, were prepared from 4 - (isobutyryl-amino)-piperidine hydrochloride and ω-chloro-p-fluoro-butyrophenone.

EXAMPLE 5

Using a procedure analogous to that described in Example 1, N-[3'-p-fluoro-benzoyl)-n-propyl]-4-(n-valeroyl-amino) -piperidine and its hydrochloride, m.p. 169°–174° C, were prepared from 4-(n-valeroyl-amino)-piperidine hydrochloride and ω-chloro-p- fluoro-butyrophenone.

EXAMPLE 6

Using a procedure analogous to that described in Example 1, N-[3'-(p-fluoro-benzoyl)-n-propyl]-4-(isovaleroyl-amino) -piperidine and its hydrochloride, m.p. 160°–164° C, were prepared from 4-(isovaleroyl-amino)-piperidine hydrochloride and ω-chloro-p-fluoro-butyrophenone.

EXAMPLE 7

Using a procedure analogous to that described in Example 1, N-[3'-(p-fluoro-benzoyl)-n-propyl]-4-(α-methylbutyryl-amino) -piperidine and its hydrochloride, m.p. 222°–226° C. were prepared from 4-(α-methyl-butyryl-amino)-piperidine hydrochloride and ω-chloro-p-fluoro-butyrophenone.

EXAMPLE 8

Using a procedure analogous to that described in Example 1, N-[3'(p-fluoro-benzoyl)-n-propyl]-4-(tert.-valeroyl-amino) -piperidine and its hydrochloride, m.p. 241°–243° C, were prepared from 4-(tert.valeroyl-amino)-piperidine hydrochloride and ω-chloro-p-fluoro-butyrophenone.

The compounds of the present invention, that is, those embraced by formula I above and their non-toxic, pharmacologically acceptable acid addition salts, have useful pharmacodynamic properties. More particularly, the compounds of this invention exhibit the characteristic desirable activity picture of neuroleptics in warm-blooded animals, such as mice and rats, and are therefore useful as CNS-depressants, sedatives and tranquilizers.

Those compounds of the formula I wherein R is methyl, ethyl and isopropyl and the structurally most closely related compound disclosed in the prior art, namely 1-[4-(4-fluorophenyl)-4-oxobutyl]-4-benzamidopiperidine disclosed in British patent specification No. 1,345,872, were tested for adrenaline-antagonistic activity, inhibition of locomotion, inhibition of exploration and toxicity by standard pharmacological test methods, and in each case the median effective dose ($ED_{50}$) or the median lethal dose ($LD_{50}$), respectively, were calculated graphically from dose-activity graphs. Albino mice (NMRI) having a body weight of 20-25 gm were used as the test animals, 10 animals per dose and untreated controls. The test compounds were administered orally in suspension in olive oil or gum arabic.

Test Procedures

1. The adrenaline-antagonistic activity was determined by the method of P.A.J. Janssen et al, Arzneimittelforschung (Drug Research) 13, 203 (1963). activity, inhibition of locomotion, inhibition of exploration and toxicity by standard pharmacological test methods, and in each case the median effective dose ($ED_{50}$) or the median lethal dose ($LD_{50}$), respectively, were calculated graphically from dose-activity graphs. Albino mice (NMRI) having a body weight of 20-25 gm were used as the test animals, 10 animals per dose and untreated controls. The test The $ED_{50}$ is the dose which produces a 50% protection against a lethal dose of adrenaline (epinephrine).

2. The inhibiting effect on exploration was determined by the method of J.R. Borssin et al, Therapie 19, 571 (1964). The $ED_{50}$ is the dose which produces a 50% decrease of exploration in the Planche-a-Trous situation.

3. The inhibiting effect on locomotion was determined by the method of P.A.J. Janssen et al, Psychopharmacologia 1, 389 (1960). The $ED_{50}$ is the dose which produces a 50% attenuation of locomotion in the open field test.

4. The toxicity was determined over an observation period of 24 hours. The $LD_{50}$ was calculated by the method J.T. Litchfield and F. Wilcoxon, J. Pharm. Exp. Ther. 96, 99 (1949).

The following table shows the results obtained:

$$R-CO-NH-\langle N-CH_2-CH_2-CH_2-CO-\langle\rangle-F$$

| Species | Test | R= CH$_3$ | R= C$_2$H$_5$ | R= i-C$_3$H$_7$ | R= C$_6$H$_5$ |
|---|---|---|---|---|---|
| Mouse | Adrenaline-antagonism ($ED_{50}$, mgm/kg) | 0.06 | 0.1 | 0.58 | 3.3 |
| Mouse | Inhibition of Exploration ($ED_{50}$, mgm/kg) | 8 | 4.4 | 9 | 45 |
| Mouse | Inhibition of Locomotion ($Ed_{50}$, mgm/kg) | 4 | 6 | 10 | 135 |
| Mouse | Toxicity ($LD_{50}$, mgm/kg) | 1050 | 1160 | 1850 | 300 |

The values tabulated above clearly show that the compounds of the instant invention are significantly more effective and less toxic than the prior art compound.

For pharmaceutical purposes the compounds according to the present invention are administered to warm-blooded animals perorally, parenterally or rectally as active ingredients in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0083 to 0.167 mgm/kg body weight, preferably 0.016 to 0.084 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 9

Coated Pills

The pill core composition is compounded from the following ingredients:

| | |
|---|---|
| N-[3'-(p-Fluoro-benzoyl)-n-propyl]-4-(acetyl-amino)-piperidine hydrochloride | 2.0 parts |
| Lactose | 28.5 parts |
| Corn starch | 17.0 parts |
| Gelatin | 2.0 parts |
| Magnesium stearate | 0.5 parts |
| Total | 50.0 parts |

Preparation

The piperidine compound is ultimately admixed with the lactose and the corn starch, the mixture is moistened with an aqueous 10% solution of the gelatin, and the moist mass is granulated by forcing it through a 1 mm-mesh screen. The granulate thus obtained in dried at 40° C, again passed through the screen and admixed with the magnesium stearate, and the composition is compressed into 50 mgm pill cores which are subsequently coated with a thin shell consisting of a mixture of sugar, titanium dioxide, talcum and gum arabic, and finally polished with beeswax. Each coated pill contains 2 mgm of the piperidine compound and is an oral dosage unit composition with effective neuroleptic action.

EXAMPLE 10

Tablets

The tablet composition is compounded from the following ingredients:

| | |
|---|---|
| N-[3'-(p-Fluoro-benzoyl)-n-propyl]-4-(propionyl-amino)-piperidine hydrochloride | 2.0 parts |
| Lactose | 55.0 parts |
| Corn starch | 38.0 parts |
| Soluble starch | 4.0 parts |
| Magnesium stearate | 1.0 parts |
| Total | 100.0 parts |

Preparation

The piperidine compound and the magnesium stearate are intimately admixed with each other, the mixture is moistened with an aqueous solution of the soluble starch and granulated as described in the preceding example, the granulate is dried and then intimately admixed with the lactose and the corn starch, and the composition is compressed into 100 mgm-tablets in a conventional table making machine. Each tablet contains 2 mgm of the piperidine compound and is an oral dosage unit composition with effective neuroleptic action.

EXAMPLE 11

Suppositories

The suppository composition is compounded from the following ingredients:

| | |
|---|---|
| N-[3'-(p-Fluoro-benzoyl)-n-propyl]-4-(butanoyl-amino)-piperidine hydrochloride | 1.0 parts |
| Suppository base (e.g. cocoa butter) | 1699.0 parts |
| Total | 1700.0 parts |

Preparation

The suppository base is melted and cooled to 40° C, the finely powdered piperidine compound is blended into the suppository base with the aid of an immersion homogenizer, and 1700 mgm-portions of the composition are poured into cooled suppository molds and allowed to harden therein. Each suppository contains 1 mgm of the piperidine compound and is a rectal dosage unit composition with effective neuroleptic action.

EXAMPLE 12

Hypodermic Solution

The solution is compounded from the following ingredients:

| | |
|---|---|
| N-[3'-(p-Fluoro-benzoyl)-n-propyl]-4-(isobutanoyl-amino)-piperidine hydrochloride | 2.0 parts |
| Sodium chloride | 18.0 parts |
| Distilled water q.s.ad | 200.0 parts by vol. |

Preparation

The piperidine compound and the sodium chloride are dissolved in the distilled water, the solution is filtered until free from suspended particles, and the filtrate is filled into 2 cc-ampules under aseptic conditions, which are subsequently sterilized and sealed. Each ampule contains 2 mgm of the piperidine compound, and its contents are an injectable dosage unit composition with effective neuroleptic action.

Analogous results are obtained when any one of the other piperidine compounds embraced by formula I or a non-toxic, pharmacologically acceptable acid addition salt thereof is substituted for the particular piperidine compound in Examples 9 through 12. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

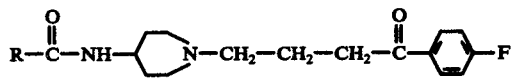

wherein R is alkyl of 1 to 4 carbon atoms, or a non-toxic, pharmacologically acceptable acid addition salt thereof.

2. A compound of claim 1, which is N-[3'-(p-fluoro-benzoyl)-n-propyl]-4-(acetyl-amino)-piperidine or a non-toxic, pharmacologically acceptable acid addition salt thereof.

3. A compound of claim 1, which is N-[3'-(p-fluoro-benzoyl)-n-propyl]-4-(propionyl-amino)-piperidine or a non-toxic, pharmacologically acceptable acid addition salt thereof.

4. A compound of claim 1, which is N-[3'-(p-fluoro-benzoyl)-n-propyl]-4-(butanoyl-amino)-piperidine or a nontoxic, pharmacologically acceptable acid addition salt thereof.

5. A compound of claim 1, which is N-[3'-(p-fluoro-benzoyl)-n-propyl]-4-(isobutanoyl-amino)-piperidine or a non-toxic, pharmacologically acceptable acid addition salt thereof.

6. A compound of claim 1, which is N-[3'-(p-fluoro-benzoyl)-n-propyl]-4-(pentanoyl-amino)-piperidine or a non-toxic, pharmacologically acceptable acid addition salt thereof.

7. A compound of claim 1, which is N-[3'-(p-fluoro-benzoyl)-n-propyl]-4-(isopentanoyl-amino)-piperidine or a non-toxic, pharmacologically acceptable acid addition salt thereof.

8. A compound of claim 1, which is N-[3'-(p-fluoro-benzoyl)-n-propyl]-4-(tert. pentanoyl-amino)-piperidine or a non-toxic, pharmacologically acceptable acid addition salt thereof.

9. A neuroleptic pharmaceutical dosage unit composition consisting essentially of an inert pharmaceutical carrier and an effective CNS-depressing, sedative or tranquilizing amount of a compound of claim 1.

10. The method of depressing the central nervous system of a warm-blooded animal in need of such treatment, which comprises perorally, parenterally or rectally administering to said animal an effective CNS-depressing, sedative or tranquilizing amount of a compound of claim 1.

UNITED STATES PATENT OFFICE
CERTIFICATE OF CORRECTION

Patent No. 4,069,331          Dated January 17, 1978

Inventor(s) ADOLF LANGBEIN, PETER DANNEBERG, FRANZ JOSEF KUHN

It is certified that error appears in the above-identified patent and that said Letters Patent are hereby corrected as shown below:

Col. 4, lines 48 thru 56 delete "activity, inhibition of locomotion, inhibition of exploration and toxicity by standard pharmacological test methods, and in each case the median effective dose ($ED_{50}$) or the median lethal dose ($LD_{50}$), respectively, were calculated graphically from dose-activity graphs. Albino mice (NMRI) having a body weight of 20-25 gm were used as test animals, 10 animals per dose and untreated controls. The test"

Col. 6, line 29 delete "table"  insert --tablet--

Signed and Sealed this

Sixteenth Day of May 1978

[SEAL]

Attest:

RUTH C. MASON
Attesting Officer

LUTRELLE F. PARKER
Acting Commissioner of Patents and Trademarks